United States Patent [19]

Fishbein et al.

[11] Patent Number: 5,059,422

[45] Date of Patent: Oct. 22, 1991

[54] CONTINUOUS RELEASE PHENYLETHANOLAMINE DERIVATIVE COMPOSITIONS

[75] Inventors: Richard Fishbein, Skillman; Susan M. Cady, Yardley; Ajit K. Chaudhuri, Somerville, all of N.J.

[73] Assignee: American Cyanamid Company, Stamford, Conn.

[21] Appl. No.: 543,237

[22] Filed: Jun. 25, 1990

Related U.S. Application Data

[63] Continuation of Ser. No. 231,640, Aug. 11, 1988, which is a continuation of Ser. No. 759,702, Jul. 29, 1985, abandoned.

[51] Int. Cl.$^5$ .................... A01N 33/02; A01N 25/34; A61K 47/00; A61K 31/135
[52] U.S. Cl. .................... 424/426; 424/422; 424/424; 424/425; 514/649; 514/653; 514/777; 514/782
[58] Field of Search ............... 424/422, 424, 425, 426, 424/485, 488; 514/2, 731, 777, 782, 649, 653

[56] References Cited

U.S. PATENT DOCUMENTS

| | | | |
|---|---|---|---|
| 2,517,513 | 8/1950 | Vaernet | 424/424 |
| 3,536,712 | 10/1970 | Keck et al. | 564/363 |
| 4,404,222 | 9/1983 | Baker et al. | 514/238.8 |
| 4,407,819 | 10/1983 | Kiernan et al. | 514/24 |
| 4,552,897 | 2/1983 | Asato | 514/554 |

FOREIGN PATENT DOCUMENTS

| | | |
|---|---|---|
| 0013949 | 8/1980 | European Pat. Off. . |
| 0049728 | 4/1982 | European Pat. Off. . |
| 81305426.9 | 5/1982 | European Pat. Off. . |
| 82300416.3 | 8/1982 | European Pat. Off. . |
| 0080595 | 8/1983 | European Pat. Off. . |
| 103830 | 3/1984 | European Pat. Off. . |
| 0008715 | 3/1989 | European Pat. Off. . |
| 2157040 | 5/1973 | Fed. Rep. of Germany . |
| 2261914 | 6/1974 | Fed. Rep. of Germany . |
| 2804625 | 8/1979 | Fed. Rep. of Germany . |
| 3306159 | 8/1984 | Fed. Rep. of Germany . |
| 83619 | 7/1977 | Japan . |
| 7303612 | 9/1973 | Netherlands . |

OTHER PUBLICATIONS

Remington's Pharmaceutical Sciences, 15th ed., pp. 1618–1635 (1975).
Chem. Abstracts, 87:201061r.
Chem. Abstracts, 100:126925g (1984).
Blodinger, Formulation of Veterinary Dosage Forms, Marcel Dekker, Inc., New York & Basel, pp. 124, 125, 160 & 161 (1983).

*Primary Examiner*—Thurman K. Page
*Assistant Examiner*—Carlos Azpuru
*Attorney, Agent, or Firm*—Alice C. Brennan

[57] ABSTRACT

The invention relates to compositions for the parenteral administration of an essentially uniform and continuous amount of a phenylethanolamine derivative over an extended period of time. The invention also relates to the preparation and administration of said compositions.

16 Claims, No Drawings

CONTINUOUS RELEASE PHENYLETHANOLAMINE DERIVATIVE COMPOSITIONS

This is a continuation of application Ser. No. 07/231,640, filed Aug. 11, 1988, which is a continuation of application Ser. No. 6/759,702, filed July 29, 1985, now abandoned.

BACKGROUND OF THE INVENTION

The difficulties encountered in the development of methods and compositions which continuously release pharmaceutical preparations in a uniform manner over extended periods of time are well known (see, for example, Remington's Pharmaceutical Sciences, 15th Edition (1975), pages 1618-1635).

Recent developments in the area of controlling the release of drugs are disclosed in European Patent Application 81305426.9 and European Patent Application 82300416.3 which describe methods for controlling the release of drugs by microencapsulation and containment within a biodegradable matrix, respectively.

Substitution products of 1-(amino-dihalophenyl)-2-aminoethanes and the acid addition salts thereof are disclosed in U.S. Pat. No. 3,536,712, issued Oct. 27, 1970, as useful agents for enhancing the blood circulation, and as bronchodilators, analgesics, sedatives, antipyretics, antiphlogistics and antitussives in warm-blooded animals. The preparation of other related 1-(amino-dihalophenyl)-2-aminoethanols and their derivatives are disclosed in Japanese Kokai 77 83,619 (Chemical Abstracts, 87,201061r), German Offenlegungsschrift 2,804,625 (1979), German Offlegungsschrift 2,157,040 (1973), German Offelegungsschrift 2,261,914 (1974), European Patent Application 8,715 (1980) and Netherlands Patent Application 7,303,612 (1973). These applications disclose uses selected from analgesics, broncholytic, antiinflammatory, uterine spasmolytic, $\beta$-mimetic and/or $\beta$-blocking activities, antispasmolytic activity on cross-striped muscle structure, for tocology, reducing blood pressure by peripheral vasodilation and mobilizing body fat, and for treating allergies.

Certain phenylethanolamine derivatives and their use for the depression of fat deposition in warmblooded animals are disclosed in U.S. Pat. No. 4,407,819. U.S. Pat. No. 4,404,222 discloses certain phenylethanolamine derivatives and their use for enhancing the growth rate of meat-producing animals and improving the efficiency of feed utilization in animals so treated. Recently, Offenlegungsschrift DE 3,306,159 A1 (European Patent Application 103830) was published describing substituted phenylethylamine derivatives which were said to be growth promoters for pigs, cows, poultry, cats, dogs, rabbits, fur animals, fish, and reptiles. The copending application for U.S. patent, Ser. No. 714,240, of Goro Asato and Terence James Bentley, filed Mar. 21, 1985, discloses certain phenylethanolamine derivatives which advantageously exhibit low $\beta_1$ heart stimulant activity which provide improved margin of safety in their use.

SUMMARY OF THE INVENTION

The present invention provides a novel composition for the parenteral administration of an essentially uniform and continuous amount of a phenylethanolamine derivative over an extended period of time comprising a compacted and partially coated phenylethanolamine derivative, which exhibits some degree of solubility in an aqueous physiological environment. The phenylethanolamine derivative suitable for use in this composition is a Formula I compound, having the structure:

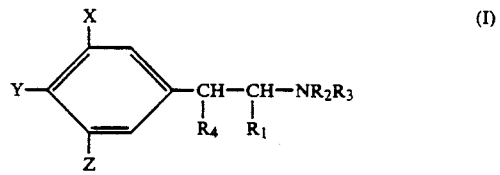

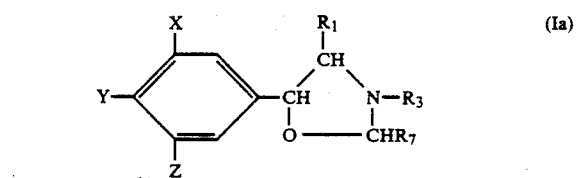

and

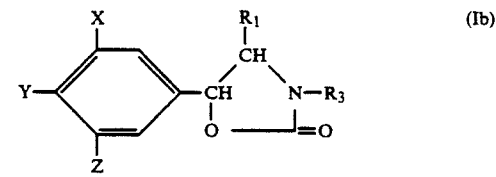

wherein,

X is hydrogen, halogen or —CN;

Y is hydrogen, $NR_8R_9$ or $NHCOR_5$;

Z is hydrogen, halogen, OH, CN, $CF_3$, $COOR_1$, $CONH_2$, $C_1$-$C_4$ alkyl, $C_1$-$C_4$ alkoxy, $NO_2$, $C_1$-$C_4$-dialkylaminomethyl or hydroxymethyl;

$R_1$ is hydrogen or $C_1$-$C_4$ alkyl;

$R_2$ is hydrogen, $C_1$-$C_6$ alkyl, $C_3$-$C_4$ alkenyl, $C_2$-$C_5$ alkanoyl or

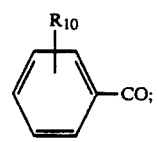

$R_3$ is hydrogen, $C_1$-$C_6$ alkyl, $C_3$-$C_6$ cycloalkyl, methoxypropyl, $C_3$-$C_4$ alkenyl, phenyl, 2-hydroxyethyl, $\alpha,\alpha$-dimethylphenethyl, benzyl, 3-phenylpropyl or 3-(4-carbomethoxyphenyl)propyl; and when $R_2$ and $R_3$ are taken together with the nitrogen to which they are attached, they represent morpholino or N'-$C_1$-$C_4$ alkylpiperazino;

$R_4$ is hydrogen, OH, $OR_6$ or $SR_{11}$;

$R_5$ is hydrogen, $C_1$-$C_4$ alkyl, $C_1$-$C_4$ alkoxy,

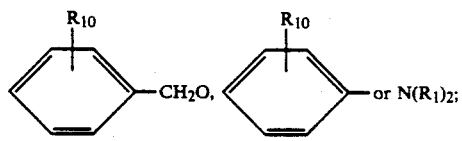

$R_6$ is $C_1$-$C_6$ alkyl, $C_2$-$C_5$ alkanoyl,

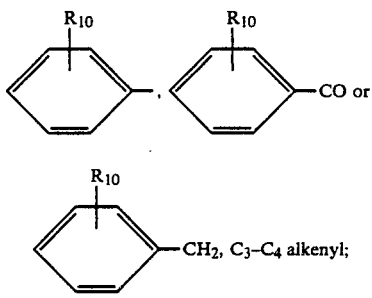

$R_7$ is hydrogen, $C_1$-$C_4$ alkyl or phenyl;

$R_8$ is hydrogen, $C_1$-$C_4$ alkyl or $C_3$-$C_4$ alkenyl;

$R_9$ is hydrogen, $C_1$-$C_6$ alkyl, $C_4$-$C_6$ cycloalkyl, $C_3$-$C_4$ alkenyl, or benzyl; and when $R_8$ and $R_9$ are taken together with the nitrogen to which they are attached, they represent pyrrolidino;

$R_{10}$ is chloro, dichloro, methyl, dimethyl, methoxy, dimethoxy or nitro; and $R_{11}$ is $C_1$-$C_6$ alkyl, phenyl or benzyl; and/or its $C_{10}$-$C_{20}$ fatty acid salt.

Surprisingly, it has been found that the partially coated implant of compacted free base Formula (I) compounds and $C_{10}$-$C_{20}$ fatty acid salts thereof show a more constant release of the compound while the uncoated implant of the free base Formula (I) compound and $C_{10}$-$C_{20}$ fatty acid salts thereof do not show a constant release of the compound.

The invention also is directed to the preparation and administration of said compositions.

PREFERRED EMBODIMENT OF THE INVENTION

The rate of release and dosage of the composition of the invention may be adjusted by the use of the pure Formula (I) compounds or fatty acid salts thereof and coating materials.

A preferred group of compounds for use in this invention have the above Formula (I) structure wherein X is hydrogen or halogen; Y is hydrogen, $NR_8R_9$ or $NHCOR_5$; Z is halogen, OH, CN, $CF_3$, $COOR_1$, $CONH_2$, methyl, methoxy, $NO_2$, $C_1$-$C_4$ dialkylaminomethyl, or hydroxymethyl; and the remaining groups are as hereinbefore defined.

A preferred group of fatty acid salts for use in this invention include the $C_{10}$-$C_{20}$ fatty acid salts of the Formula I compounds.

The composition of the invention may optionally contain up to about 50% by weight of a diluent or mixture of diluents and up to about 5% by weight of a lubricant or mixture of lubricants. Suitable diluents for the invention are ethyl cellulose and castorwax. A suitable lubricant for the invention is magnesium stearate.

The term "aqueous physiological environment" means the body of a warm-blooded animal as well as such an in vitro environment which may be mimicked by aqueous liquids, such as phosphate buffered solutions at a temperature of 35° to 40° C.

An implant for the administration of phenylethanolamine derivatives may be prepared by admixing a Formula (I) compound in an organic solvent such as methanol, optionally with a fatty acid, if a salt is desired, and then adding the ethyl cellulose and castorwax. The resulting material is isolated by removing the solvent and drying. The isolated material is ground to a fine powder and is pressed by compaction or extrusion into an implant, preferably a cylindrical implant. The compacted material is coated with a biodegradable or non-biodegradable coating by conventional techniques. Prior to implantation a specified area of the coating is removed to expose the compacted drug. For example, the coating may be cut off at one or both of the ends of a cylindrical implant.

It has been shown in an in vivo sheep study that the desirable dissolution characteristics of the compositions of the invention are maintained and that the release profiles for in vivo release and in vitro dissolution are comparable, demonstrating the effectiveness of the present compositions for the parenteral administration of Formula (I) phenylethanolamine derivatives. In a controlled experiment, a compacted ⅛" cylindrical implant, containing 50% on a weight basis of a Formula (I) phenylethanolamine compound previously described, 45% on a weight basis of castorwax, and 5% on a weight basis of ethylcellulose, and coated with a non-biodegradable coating, released 0.11 mg/day to 1.28 mg/day of said phenylethanolamine compound from the implant in vivo, compared to 0.13 mg/day to 0.82 mg/day in vitro.

The invention is further illustrated by the following non-limiting examples.

EXAMPLES 1-10

Preparation of salts of phenylethanolamine derivatives

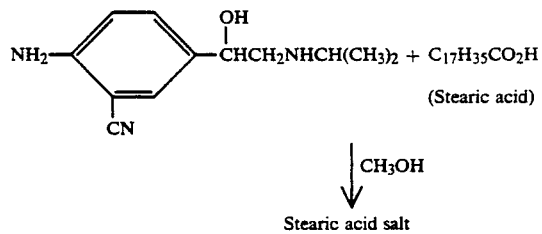

(Stearic acid)

↓ $CH_3OH$

Stearic acid salt

5-[1-Hydroxy-2-(isopropylamino)ethyl] anthranilonitrile (0.7458 g, 0.00262 mol) and stearic acid (1.04 molar equivalents) are added to hot methyl alcohol (6 g) and the resulting solution is stirred at reflux for one hour. The resulting mixture is cooled and the methyl alcohol is removed under reduced pressure. The resulting molten material, which solidified on standing, is ground to a fine powder, and dried in a vacuum, and further dried in a vacuum oven at 55° C. The resulting solid is washed with several aliquots of anhydrous diethyl ether to remove excess stearic acid, and is dried to give 1.016 g, 88.5% yield of the desired salt.

Salts of the phenylethanolamine derivatives are prepared using the above procedure and the appropriate phenylethanolamines and organic acids. Table I contains an elemental analysis of ten phenylethanolamine derivatives.

TABLE I

Elemental analysis of different phenylethanolamine salts

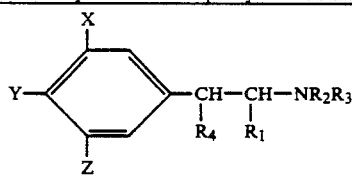

| Example No | $R_1$ | $R_2$ | $R_3$ | $R_4$ | X | Y | Z | Salt type | Found %C | Found %H | Found %N | Calculated %C | Calculated %H | Calculated %N |
|---|---|---|---|---|---|---|---|---|---|---|---|---|---|---|
| 1 | H | H | i-$C_3H_7$ | OH | H | $NH_2$ | CN | Stearate | 71.46 | 10.47 | 8.41 | 71.57 | 10.54 | 8.35 |
| 2 | H | H | i-$C_3H_7$ | OH | H | $NH_2$ | CN | Caproate | 64.52 | 8.29 | 12.26 | 64.40 | 8.64 | 12.52 |
| 3 | H | H | i-$C_3H_7$ | OH | H | $NH_2$ | CN | Benzoate | 64.14 | 6.42 | 11.98 | 66.78 | 6.74 | 12.30 |
| 4 | H | H | i-$C_3H_7$ | OH | H | $NH_2$ | CN | Pamoate | 64.66 | 5.92 | 9.07 | 68.20 | 6.05 | 10.16 |
| 5 | H | H | i-$C_3H_7$ | OH | H | $NH_2$ | CN | Myristate | 69.95 | 9.81 | 9.06 | 69.69 | 10.05 | 9.38 |
| 6 | H | H | i-$C_3H_7$ | OH | H | $NH_2$ | CN | Fumarate | 59.31 | 6.70 | 14.53 | 60.58 | 6.85 | 15.14 |
| 7 | H | H | t-$C_4H_9$ | OH | Cl | $NH_2$ | Cl | Myristate | 61.12 | 8.40 | 5.53 | 61.79 | 9.11 | 5.55 |
| 8 | H | H | t-$C_4H_9$ | OH | Cl | $NH_2$ | Cl | Stearate | 64.80 | 7.87 | 4.99 | 64.18 | 9.63 | 4.99 |
| 9 | H | H | t-$C_4H_9$ | OH | F | H | CN | Myristate | 70.11 | 9.28 | 6.03 | 69.83 | 9.70 | 6.03 |
| 10 | H | H | t-$C_4H_9$ | OH | F | H | CN | Stearate | 72.03 | 10.25 | 5.44 | 71.54 | 10.19 | 5.38 |

EXAMPLE 11

Preparation of the partially coated compacted implants of phenylethanolamine derivatives Implants are prepared by weighing a sufficient quantity of the ground homogeneous mixture of the desired salt or of pure phenylethanolamine and the desired diluents. The mixture is then compressed on a carver press at from 1000 to 5000 psig in a 3/16" or ¼" diameter cylindrical die. Smaller implants are prepared by compressing the appropriate quantity of the compound or acid salt on a rotary tablet press using a ⅛" diameter punch and die to give cylindrical implants.

The implants prepared above are coated with both biodegradable and non-biodegradable coatings by procedures A and B below.

PROCEDURE A

Non-Biodegradable Silicon Polymer

Clean grade silicon elastomer (10 parts) is mixed with curing agent (one part) on a watch glass with a spatula. This mixture is deaerated in a dessicator for 30 minutes. The implants are grasped by the ends with tweezers, rolled into the silicon polymer, placed on end on aluminum foil and cured at 40° C. overnight. One or both of the ends are removed with a razor blade leaving the "shaft" of the cylinder coated.

Alternatively, implants may be dip coated with 20% to 40% of a medical adhesive, sold under the trademark SILASTIC® by Dow Corning, which has been dispersed in hexane, and dried and cured at 40° C. to 50° C. overnight before removing the coating from one or both of the base ends.

PROCEDURE B

Biodegradable Coatings

The polymer or copolymer (one part) is dissolved in chloroform (three to eight parts). Each implant is grasped by the ends with tweezers, dipped into the polymer solution, and then the chloroform evaporated at room temperature. After the coating dries overnight at room temperature, the polymer ends are removed with a razor blade, leaving the long cylindrical "shaft" coated.

Table II below contains a summary of the physical data on the coated implants thus prepared.

TABLE II

| Implant No | Example No | % Phenyl ethanolamine as free base | Magnesium stearate % | Ethyl cellulose % | Castor-wax % | Wt (mg) | Length (mm) | Coating | Surface for release (ends open) |
|---|---|---|---|---|---|---|---|---|---|
| 1 | 1 | (Free base) 80 | — | 5.0 | 15 | 58.5 | 6.6 | Non-biodegradable | 1 |
| 2 | 1 | (Free base) 70 | — | 5.0 | 25 | 57.5 | 6.6 | Non-biodegradable | 1 |
| 3 | 1 | (Free base) 60 | — | 5.0 | 35 | 56.9 | 6.4 | Non-biodegradable | 1 |
| 4 | 1 | (Free base) 50 | — | 5.0 | 45 | 56.9 | 6.4 | Non-biodegradable | 1 |
| 5 | 1 | (Free base) 96 | 0.5 | 3.5 | — | 52.0 | ~6.0 | Biodegradable | 2 |
| 6 | 1 | (Free base) 96 | 0.5 | 3.5 | — | 54.0 | ~6.0 | Non-biodegradable | 1 |
| 7 | 1 | (Free base) 96 | 0.5 | 3.5 | — | 54.0 | ~6.0 | Biodegradable | 1 |
| 8 | 1 | (Free base) 96 | 0.5 | 3.5 | — | 52.0 | ~6.0 | Non-biodegradable | 2 |
| 9 | 1 | (Stearate) 96 | — | 4.0 | — | 54 | 6.2 | Non-biodegradable | 1 |
| 10 | 1 | (Stearate) 96 | — | 4.0 | — | 54.0 | 6.2 | Non-biodegradable | 2 |

TABLE II-continued

| Implant No | Example No | % Phenyl ethanolamine as free base | Magnesium stearate % | Ethyl cellulose % | Castor-wax % | Wt (mg) | Length (mm) | Coating | Surface for release (ends open) |
|---|---|---|---|---|---|---|---|---|---|
| 11 | 2 | (Caproate) 95 | 1.0 | 3.5 | — | ~59.5 | ~6.0 | Non-biodegradable | 1 |
| 12 | 3 | (Benzoate) 95 | 1.0 | 3.5 | — | 60.4 | ~6.0 | Non-biodegradable | 1 |
| 13 | 4 | (Pamoate) 95 | 1.0 | 3.5 | — | 49.4 | ~6.0 | Non-biodegradable | 1 |
| 14 | 5 | (Myrisate) 95 | 1.0 | 3.5 | — | ~61.4 | ~6.0 | Non-biodegradable | 1 |
| 15 | 6 | (Fumarate) 95 | 1.0 | 3.5 | — | 57.5 | ~6.0 | Non-biodegradable | 1 |
| 16 | 7 | (Myristate) 50 | — | 5.0 | 45.0 | 62.5 | 7.0 | Non-biodegradable | 1 |
| 17 | 8 | (Stearate) 50 | — | 5.0 | 45.0 | 64.0 | 7.5 | Non-biodegradable | 1 |
| 18 | 7 | (Free base) 50 | — | 5.0 | 45.0 | 63.0 | — | Non-biodegradable | 1 |
| 19 | 9 | (Myristate) 50 | — | 5.0 | 45.0 | 62.8 | 7.2 | Non-biodegradable | 1 |
| 20 | 10 | (Stearate) 50 | — | 5.0 | 45.0 | 63.4 | 7.4 | Non-biodegradable | 1 |
| 21 | 9 | (Free base) 50 | — | 5.0 | 45.0 | 58.0 | — | Non-biodegradable | 1 |
| 22 | 7 | (Myristate) 95 | 1.0 | 4.0 | — | 63.2 | 7.0 | Non-biodegradable | 1 |

EXAMPLE 12

Dissolution Experiments

Dissolution experiments are carried out at 39° C. using a shaking bottle method. Phosphate buffered saline (PBS) adjusted to pH - 7.1 is the dissolution medium ($NaH_2PO_4 \cdot H_2O$ 3.45 g, $Na_2HPO_4$ 3.55 g NaCl 9.50 g dissolved in distilled water to 1000 mL).

The implant is placed in a disposable polypropylene flat base tube (Sarstedt No 58.537 with No 67.790 cap) and 30 mL PBS is added. The tubes are placed in a 39° C. Fisher Shaking Water Bath (Model 129 — shaker setting a 2¾). The PBS is changed daily, with each measurement and samples are assayed by optical density measurement at 321 nm or 287 nm to give the dissolution profiles.

The results of these experiments are summarized in Tables III, IV, and V below. Table III shows the dissolution of uncoated compacted implants of pure Formula I compounds in an aqueous physiological environment at 39° C. from 11 to 17 days. The dissolution kinetics and rate are altered by coating the cylindrical implant and having one or both of the ends exposed. Table IV illustrates the improvement in dissolution profiles of the implants obtained with biodegradable and non-biodegradable coating material. The use of free bases and different $C_{10}$–$C_{20}$ fatty acid salts in conjunction with diluents and various coatings on the compacted implants provides a means of regulating the release rate of the compounds over extended periods of time. Table V represents the variations in the release profiles obtained with various salts of Formula I compounds having the structure

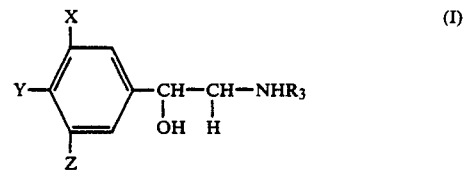

(I)

wherein $R_3$ is i-$C_3H_7$ or t-$C_4H_9$; X is hydrogen or halogen; Y is hydrogen or $NH_2$; Z is halogen or CN, obtained with non-biodegradable coating material.

TABLE III

Dissolution of uncoated compacted implants of Formula I Compounds $$Y-\underset{Z}{\overset{X}{\underset{|}{\bigcirc}}}-\underset{OH}{\overset{|}{C}H}-\underset{H}{\overset{|}{C}H}-NH_2R_3$$

| Compound | | | | | Castor wax % | Ethyl-cellulose % | Range of release mg/day | Days until exhausted |
|---|---|---|---|---|---|---|---|---|
| $R_3$ | X | Y | Z | % | | | | |
| i-$C_3H_7$ | H | $NH_2$ | CN | 80 | 15 | 5 | 1.53–14.52 | 11 |
| i-$C_3H_7$ | H | $NH_2$ | CN | 70 | 25 | 5 | 1.79–13.1 | 11 |
| i-$C_3H_7$ | H | $NH_2$ | CN | 60 | 35 | 5 | 0.22–11.21 | 12 |
| i-$C_3H_7$ | H | $NH_2$ | CN | 50 | 45 | 5 | 0.56–9.49 | 14 |
| t-$C_4H_9$ | Cl | $NH_2$ | Cl | 50 | 45 | 5 | 0.38–8.71 | 17 |

TABLE IV

Dissolution of partially coated compacted implants of Formula I compounds

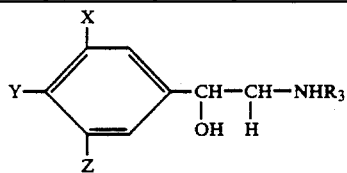

| Compound | | | | | Magnesium Stearate | Castor wax | Ethyl cellulose | | Surface for release | Range of release | Days until |
|---|---|---|---|---|---|---|---|---|---|---|---|
| R$_3$ | X | Y | Z | % | % | % | % | Coating | (ends open) | mg/day | exhausted |
| i-C$_3$H$_7$ | H | NH$_2$ | CN | 80 | — | 15 | 5.0 | Non-biodegradable | 1 | .24–5.15 | 43 |
| i-C$_3$H$_7$ | H | NH$_2$ | CN | 70 | — | 25 | 5.0 | Non-biodegradable | 1 | .6–1.73 | 39 |
| i-C$_3$H$_7$ | H | NH$_2$ | CN | 60 | — | 35 | 5.0 | Non-biodegradable | 1 | 0.3–2.72 | 46 |
| i-C$_3$H$_7$ | H | NH$_2$ | CN | 50 | — | 45 | 5.0 | Non-biodegradable | 1 | 0.13–0.82 | 67 |
| i-C$_3$H$_7$ | H | NH$_2$ | CN | 96 | 0.5 | — | 3.5 | Biodegradable | 2 | 1.9–3.41 | 22 |
| i-C$_3$H$_7$ | H | NH$_2$ | CN | 96 | 0.5 | — | 3.5 | Non-biodegradable | 1 | 0.57–1.69 | 50 |
| i-C$_3$H$_7$ | H | NH$_2$ | CN | 96 | 0.5 | — | 3.5 | Biodegradable | 1 | 0.17–4.98 | 27 |
| i-C$_3$H$_7$ | H | NH$_2$ | CN | 96 | 0.5 | — | 3.5 | Non-biodegradable | 2 | 0.48–8.17 | 22 |
| t-C$_4$H$_9$ | Cl | NH$_2$ | Cl | 50 | — | 45 | 5.0 | Non-biodegradable | 1 | 0.22–0.99 | 52 |
| t-C$_4$H$_9$ | F | H | CN | 50 | — | 45 | 5.0 | Non-biodegradable | 1 | 0.2–4.43 | 17 |

TABLE V

Dissolution of partially coated compacted implants of salts of Formula I compounds

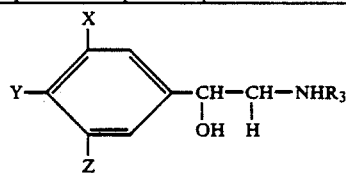

| | Compound | | | | % | Magnesium stearate | Ethyl cellulose | Castor wax | Surface for release | Range of release |
|---|---|---|---|---|---|---|---|---|---|---|
| Salt | R$_3$ | X | Y | Z | free base | % | % | % | (ends open) | mg/day |
| Stearate | i-C$_3$H$_7$ | H | NH$_2$ | CN | 96 | — | 4.0 | — | 1 | 0.07–0.35 |
| Caproate | i-C$_3$H$_7$ | H | NH$_2$ | CN | 95 | 1.0 | 4.0 | — | 1 | 1.2–29.5 |
| Benzoate | i-C$_3$H$_7$ | H | NH$_2$ | CN | 95 | 1.0 | 4.0 | — | 1 | 0.91–11.67 |
| Pamoate | i-C$_3$H$_7$ | H | NH$_2$ | CN | 95 | 1.0 | 4.0 | — | 1 | 0.4–1.87 |
| Myristate | i-C$_3$H$_7$ | H | NH$_2$ | CN | 95 | 1.0 | 4.0 | — | 1 | 0.24–2.14 |
| Fumarate | i-C$_3$H$_7$ | H | NH$_2$ | CN | 95 | 1.0 | 4.0 | — | 1 | 0.59–8.97 |
| Myristate | t-C$_4$H$_9$ | Cl | NH$_2$ | Cl | 50 | — | 5.0 | 45.0 | 1 | 0.12–0.52 |
| Stearate | t-C$_4$H$_9$ | Cl | NH$_2$ | Cl | 50 | — | 5.0 | 45.0 | 1 | 0.05–0.295 |
| Myristate | t-C$_4$H$_9$ | F | H | CN | 50 | — | 5.0 | 45.0 | 1 | 0.056–0.068 |
| Stearate | t-C$_4$H$_9$ | F | H | CN | 50 | — | 5.0 | 45.0 | 1 | 0.012–0.057 |
| Myristate | t-C$_4$H$_9$ | Cl | NH$_2$ | Cl | 95 | 1.0 | 4.0 | — | 1 | 0.17–0.57 |

EXAMPLE 14

Dissolution characteristics of a partially coated compacted implant of Carbon 14 labeled 5-[1-hydroxy-2-(isopropylamino)ethyl]anthranilonitrile I. Preparation of Carbon 14 labeled material for implant fabrication Carbon 14 labeled and cold samples of the title phenylethanolamine compound in approximately 1:9 weight ratio are dissolved in methanol and solvent removed under reduced pressure to give a homogeneous sample. Requisite amounts of C$^{14}$-labeled compound, castor wax and ethylcellulose are dissolved in methanol with heating and then the methanol is evaporated off to make two different compositions corresponding to Implant No. 2 (i.e. 70% drug, 25% castor wax, 5% ethylcellulose) and Implant No. 4 (i.e. 50% drug, 45% castor wax, 5% ethylcellulose). The residue ground to a fine powder.

II. Implant fabrication

A carver press (Model M) and ⅛" diameter cylindrical die are used to compress 71.4 mg (Implant No. 4) or 91.8 mg (Implant No. 2) of the preparation from I above at 3000 psig for ten minutes to yield a ⅛: diameter cylindrical implant. Alternatively, the implants are extruded using a laboratory Mini Max Molder (Custom Scientific Instruments) directly into a custom made ⅛ inch diameter cylindrical die.

III. Implant coating

A non-biodegradable polymer coating is applied by grasping each of the implants with tweezers and dipping into a homogeneous coating solution consisting of ten parts by weight silicon elastomer and one part by weight curing agent in 20 parts by weight of hexane. The tipped implants are then dried at room temperature for two hours and then cured at 50°–55° C. for 12 hours. The polymer coating is removed from one end by slicing, leaving a cylinder with one end surface exposed.

IV. Implant administration and release in vivo

Two white face crossbread lambs weighing 35–40 kg each housed in metabolism cages and receiving ad libitum sheep grower ration No 619 plus hay, and water ad libitum are acclimated to cages for four days before implantation. The lambs are implanted each with one implant using an implanting gun.

| Lamb | Implant No. |
| --- | --- |
| 1A | 2 |
| 1B | 4 |

The total amount of urine from each of the lambs is collected daily and samples analyzed for radioactivity with the standard AQUASOL-2 cocktail liquid scintillation fluid using a Beckman Scintillation Counter. At the completion of the experiment, the lambs are sacrificed, the implants removed and examined for physical integrity and extracted with 100 mL of methanol to determine the residual radioactivity in the implants.

The results of these experiments which are summarized in Table VI below demonstrate the effectiveness of the partially coated implant composition of phenylethanolamine derivatives for administration of these compounds in vivo. The results of these experiments also demonstrate a uniform release of drug over a period of 30 days.

TABLE VI

In vivo release of $C^{14}$-labeled phenylethanolamine implants in lambs

| Day | Implant Number 2 Amount in urine (mg) | Implant Number 4 Amount in urine (mg) |
| --- | --- | --- |
| 1 | 1.46 | 0.54 |
| 2 | 1.61 | 0.94 |
| 3 | 2.00 | 1.28 |
| 4 | 2.01 | 1.17 |
| 5 | 1.78 | 1.18 |
| 6 | 1.36 | 1.15 |
| 7 | 0.35 | 1.08 |
| 8 | 1.92 | 1.20 |
| 9 | 1.76 | 1.10 |
| 10 | 1.62 | 0.96 |
| 11 | 1.82 | 1.12 |
| 12 | 1.45 | 0.91 |
| 13 | 1.60 | 0.94 |
| 14 | 1.37 | 0.82 |
| 15 | 1.55 | 0.87 |
| 16 | 1.92 | 0.99 |
| 17 | 1.47 | 0.77 |
| 18 | 1.53 | 0.82 |
| 19 | 1.47 | 0.78 |
| 20 | 1.62 | 0.83 |
| 21 | 1.29 | 0.65 |
| 22 | 1.43 | 0.73 |
| 23 | 1.44 | 0.59 |
| 24 | 1.37 | 0.54 |
| 25 | 1.58 | 0.57 |
| 26 | 1.19 | 0.46 |
| 27 | 1.11 | 0.34 |
| 28 | 1.04 | 0.31 |
| 29 | 1.03 | 0.28 |
| 30 | 0.78 | 0.28 |
| 31 | 0.82 | 0.29 |
| 32 | 0.65 | 0.27 |

TABLE VI-continued

In vivo release of $C^{14}$-labeled phenylethanolamine implants in lambs

| Day | Implant Number 2 Amount in urine (mg) | Implant Number 4 Amount in urine (mg) |
| --- | --- | --- |
| 33 | 0.37 | 0.17 |
| 34 | 0.26 | 0.13 |
| 35 | 0.10 | 0.11 |
| 36 | 0.09 | 0.04 |
| 37 | 0.05 | 0.03 |
| 38 | 0.05 | 0.03 |
| 39 | 0.04 | 0.03 |
| 40 | 0.03 | 0.02 |

EXAMPLE 15

Efficacy of phenylethanolamine implants

Six week feed and growth performance trials are conducted using the one end open non-biodegradable coated phenylethanolamine implant number 4, each containing 26.5 mg of the drug. Treatment groups in the study includes a control implant (implants without drug) and lambs implanted with one and two implants. Each group has 5 to 33 lambs weighing 30 to 35 kg each. The implants are placed subcutaneously in the midsection of the back of the right ear, using an implanting gun. The lambs receive sheep grower ration number 619 plus hay and water ad libitum. Lambs are weighed periodically and feed intake noted and implants are removed and analyzed for remaining drug.

The results of these experiments are summarized in Table VII, which demonstrates the controlled release of phenylethanolamine obtained with the implants of the invention, and in Table VIII, which demonstrate the improvements in weight gains and feed efficiency obtained by the use of the phenylethanolamine implants of the invention.

TABLE VII

Release of phenylethanolamine from implants in vivo

| Period (day) | Average drug released mg/day/implant |
| --- | --- |
| 0–20 | 0.87 |
| 20–26 | 0.54 |
| 26–33 | 0.477 |
| 33–41 | 0.26 |
| 41–47 | 0.076 |

TABLE VIII

Effect of implant treatment on weight gain and feed efficiency

| | Control (no drug) | One Implant | Two Implants |
| --- | --- | --- | --- |
| Average daily wt. gain in grams | 178.0 | 204.0 | 231.0 |
| Average daily feed intake in kilograms | 1.35 | 1.31 | 1.37 |
| Feed intake per unit of gain | 7.64 | 6.49 | 5.96 |

What is claimed is:

1. A composition for the parenteral administration of an essentially uniform and continuous amount of a phenylethanolamine derivative over an extended period of time which comprises a compacted and partially coated admixture of a wax, a cellulose or a mixture thereof with a phenylethanolamine derivative, which exhibits some degree of solubility in an aqueous physiological environment, where the phenylethanolamine derivative is a Formula I compound, having the structure selected from the group consisting of:

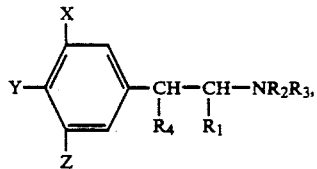  (I)

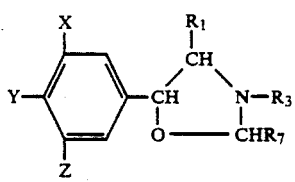  (Ia)

and

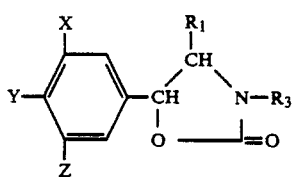  (Ib)

wherein

X is hydrogen, halogen or —CN;

Y is hydrogen, $NR_8R_9$ or $NHCOR_5$;

Z is hydrogen, halogen, OH, CN, $CF_3$, $COOR_1$, $CONH_2$, $C_1$–$C_4$ alkyl, $C_1$–$C_4$ alkoxy, $NO_2$, $C_1$–$C_4$-dialkylaminomethyl or hydroxymethyl;

$R_1$ is hydrogen or $C_1$–$C_4$ alkyl;

$R_2$ is hydrogen, $C_1$–$C_6$ alkyl, $C_3$–$C_4$ alkenyl, $C_2$–$C_5$ alkanoyl or

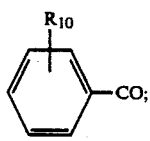

$R_3$ is hydrogen, $C_1$–$C_6$ alkyl, $C_3$–$C_6$ cycloalkyl, methoxypropyl, $C_3$–$C_4$ alkenyl, phenyl, 2-hydroxyethyl, α,α-dimethylphenethyl, benzyl, 3-phenylpropyl or 3-(4-carbomethoxyphenyl)propyl; and when $R_2$ and $R_3$ are taken together with the nitrogen to which they are attached, they represent morpholino or $N'$-$C_1$–$C_4$ alkylpiperazino;

$R_4$ is hydrogen, OH, $OR_6$ or $SR_{11}$;

$R_5$ is hydrogen, $C_1$–$C_4$ alkyl, $C_1$–$C_4$ alkoxy,

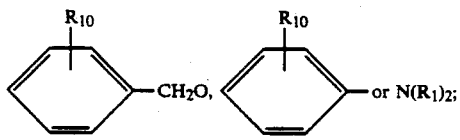

$R_6$ is $C_1$–$C_6$ alkyl, $C_2$–$C_5$ alkanoyl,

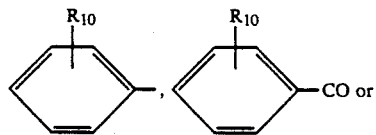

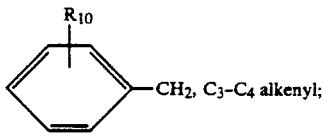

$R_7$ is hydrogen, $C_1$–$C_4$ alkyl or phenyl;

$R_8$ is hydrogen, $C_1$–$C_4$ alkyl or $C_3$–$C_4$ alkenyl;

$R_9$ is hydrogen, $C_1$–$C_6$ alkyl, $C_4$–$C_6$ cycloalkyl, $C_3$–$C_4$ alkenyl, or benzyl; and when $R_8$ and $R_9$ are taken together with the nitrogen to which they are attached, they represent pyrrolidino;

$R_{10}$ is chloro, dichloro, methyl, dimethyl, methoxy, dimethoxy or nitro; and $R_{11}$ is $C_1$–$C_6$ alkyl, phenyl or benzyl; or its $C_{10}$–$C_{20}$ fatty acid salt.

2. A composition according to claim 1, which comprises up to about 50% by weight of the wax, the cellulose or the mixture thereof.

3. A composition according to claim 1, which further comprises up to about 5% by weight of a lubricant.

4. A composition according to claim 1, wherein X is hydrogen or halogen; Y is hydrogen, $NR_8R_9$ or $NHCOR_5$; Z is halogen, OH, CN, $CF_3$, $COOR_1$, $CONH_2$, methyl, methoxy, $NO_2$, $C_1$–$C_4$ dialkylaminomethyl, or hydroxymethyl.

5. A composition according to claim 1, wherein X is hydrogen, Y is $NH_2$, Z is CN, $R_3$ is i-$C_3H_7$, $R_1$ and $R_2$ are hydrogen and $R_4$ is OH.

6. A composition according to claim 1, wherein X is Cl, Y is $NH_2$, Z is Cl, $R_3$ is t-$C_4H_9$, $R_1$ and $R_2$ are hydrogen and $R_4$ is OH.

7. A composition according to claim 1, wherein X is F, Y is hydrogen, Z is CN, $R_3$ is t-$C_4H_9$, $R_1$ and $R_2$ are hydrogen, and $R_4$ is OH.

8. A composition according to claim 1, wherein X and Y are hydrogen, Z is CN, $R_3$ is t-$C_3H_7$, $R_1$ and $R_2$ are hydrogen and $R_4$ is OH.

9. A composition according to claim 1, wherein the coating is biodegradable or nonbiodegradable.

10. A method for regulating parenterally an essentially uniform and continuous amount of a phenylethanolamine derivative over an extended period of time which comprises implanting a compacted and partially coated admixture of a wax, a cellulose or a mixture thereof with a phenylethanolamine derivative, which exhibits some degree of solubility in an aqueous physiological environment, where the phenylethanolamine derivative is a Formula I compound, having the structure selected from the group consisting of:

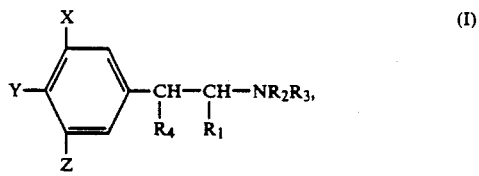  (I)

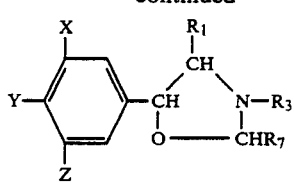

and

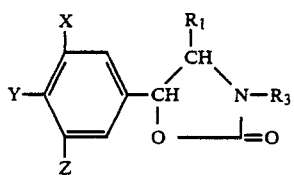

wherein

X is hydrogen, halogen or —CN;

Y is hydrogen, $NR_8R_9$ or $NHCOR_5$;

Z is hydrogen, halogen, OH, CN, $CF_3$, $COOR_1$, $CONH_2$, $C_1$-$C_4$ alkyl, $C_1$-$C_4$ alkoxy, $NO_2$, $C_1$-$C_4$-dialkylaminoethyl or hydroxymethyl;

$R_1$ is hydrogen or $C_1$-$C_4$ alkyl;

$R_2$ is hydrogen, $C_1$-$C_6$ alkyl, $C_3$-$C_4$ alkenyl, $C_2$-$C_5$ alkanoyl or

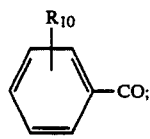

$R_3$ is hydrogen, $C_1$-$C_6$ alkyl, $C_3$-$C_6$ cycloalkyl, methoxypropyl, $C_3$-$C_4$ alkenyl, phenyl, 2-hydroxyethyl, α,α-dimethylphenethyl, benzyl, 3-phenylpropyl or 3-(4-carbomethoxyphenyl)propyl; and when $R_2$ and $R_3$ are taken together with the nitrogen to which they are attached, they represent morpholino or N'-$C_1$-$C_4$ alkylpiperazino;

$R_4$ is hydrogen, OH, $OR_6$ or $SR_{11}$;

$R_5$ is hydrogen, $C_1$-$C_4$ alkyl, $C_1$-$C_4$ alkoxy,

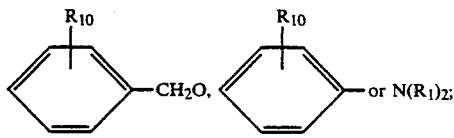

$R_6$ is $C_1$-$C_6$ alkyl, $C_2$-$C_5$ alkanoyl,

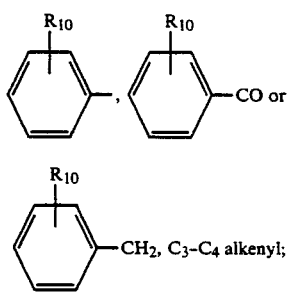

$R_7$ is hydrogen, $C_1$-$C_4$ alkyl or phenyl;

$R_8$ is hydrogen, $C_1$-$C_4$ alkyl or $C_3$-$C_4$ alkenyl;

$R_9$ is hydrogen, $C_1$-$C_6$ alkyl, $C_4$-$C_6$ cycloalkyl, $C_3$-$C_4$ alkenyl, or benzyl; and when $R_8$ and $R_9$ are taken together with the nitrogen to which they are attached, they represent pyrrolidino;

$R_{10}$ is chloro, dichloro, methyl, dimethyl, methoxy, dimethoxy or nitro; and $R_{11}$ is $C_1$-$C_6$ alkyl, phenyl or benzyl; or its $C_{10}$-$C_{20}$ fatty acid salt.

11. A method according to claim 10, wherein X is hydrogen or halogen; Y is hydrogen, $NR_8R_9$ or $NHCOR_5$; Z is halogen, OH, CN, $CF_3$, $COOR_1$, $CONH_2$, methyl, methoxy, $NO_2$, $C_1$-$C_4$ dialkylaminomethyl, or hydroxymethyl.

12. A method according to claim 10, wherein X is hydrogen, Y is $NH_2$, Z is CN, $R_3$ is i-$C_3H_7$, $R_1$ and $R_2$ are hydrogen and $R_4$ is OH.

13. A method according to claim 10, wherein X is Cl, Y is $NH_2$, Z is Cl, $R_3$ is t-$C_4H_9$, $R_1$ and $R_2$ are hydrogen and $R_4$ is OH.

14. A method according to claim 10, wherein X is F, Y is hydrogen, Z is CN, $R_3$ is t-$C_4H_9$, $R_1$ and $R_2$ are hydrogen, and $R_4$ is OH.

15. A method according to claim 10, wherein X and Y are hydrogen, Z is CN, $R_3$ is t-$C_3H_7$, $R_1$ and $R_2$ are hydrogen and $R_4$ is OH.

16. A method according to claim 10, wherein the coating is biodegradable or nonbiodegradable.

* * * * *